United States Patent [19]
Wang et al.

[11] Patent Number: 5,371,261
[45] Date of Patent: Dec. 6, 1994

[54] FULLY ALKOXYSILANE-FUNCTIONALIZED ALIPHATIC POLYAMINE COMPOUNDS

[75] Inventors: Bing Wang, Maplewood, Minn.; Garth L. Wilkes, Blacksburg, Va.

[73] Assignee: Virginia Tech Intellectual Properties, Inc., Blacksburg, Va.

[21] Appl. No.: 50,377

[22] PCT Filed: Nov. 18, 1991

[86] PCT No.: PCT/US91/08597
§ 371 Date: May 12, 1993
§ 102(e) Date: May 12, 1993

[51] Int. Cl.$^5$ .................. C07F 7/10; C08G 77/00; C08F 8/00; B32B 27/36
[52] U.S. Cl. .................. 556/421; 556/419; 556/424; 528/28; 528/41; 428/412; 428/447; 428/469; 106/287.16; 525/105
[58] Field of Search ............... 556/421, 424; 528/28, 528/41

[56] References Cited

U.S. PATENT DOCUMENTS

| | | | |
|---|---|---|---|
| 3,856,756 | 12/1974 | Wagner et al. | 260/77.5 AQ |
| 3,940,370 | 2/1976 | DiSalvo | 260/77.5 CH |
| 4,448,694 | 5/1984 | Plueddemann | 210/682 |
| 4,719,262 | 1/1988 | Plueddemann | 525/105 |
| 4,746,366 | 5/1988 | Philipp et al. | 106/287.19 |

*Primary Examiner*—Paul F. Shaver
*Attorney, Agent, or Firm*—Richard P. Fennelly; Louis A. Morris

[57] ABSTRACT

Fully alkoxysilane-functionalized aliphatic polyamine compounds (e.g., fully functionalized dialkylenetriamine compounds) can be formed by reacting a dialkylenetriamine (e.g., diethylenetriamine) with a compound comprising an amine-reactive group and an alkoxysilane group (e.g., an isocyanatoalkylalkoxysilane). These functionalized compounds find utility as the predominant component in forming organic/inorganic hybrid materials via sol-gel processing.

9 Claims, 3 Drawing Sheets

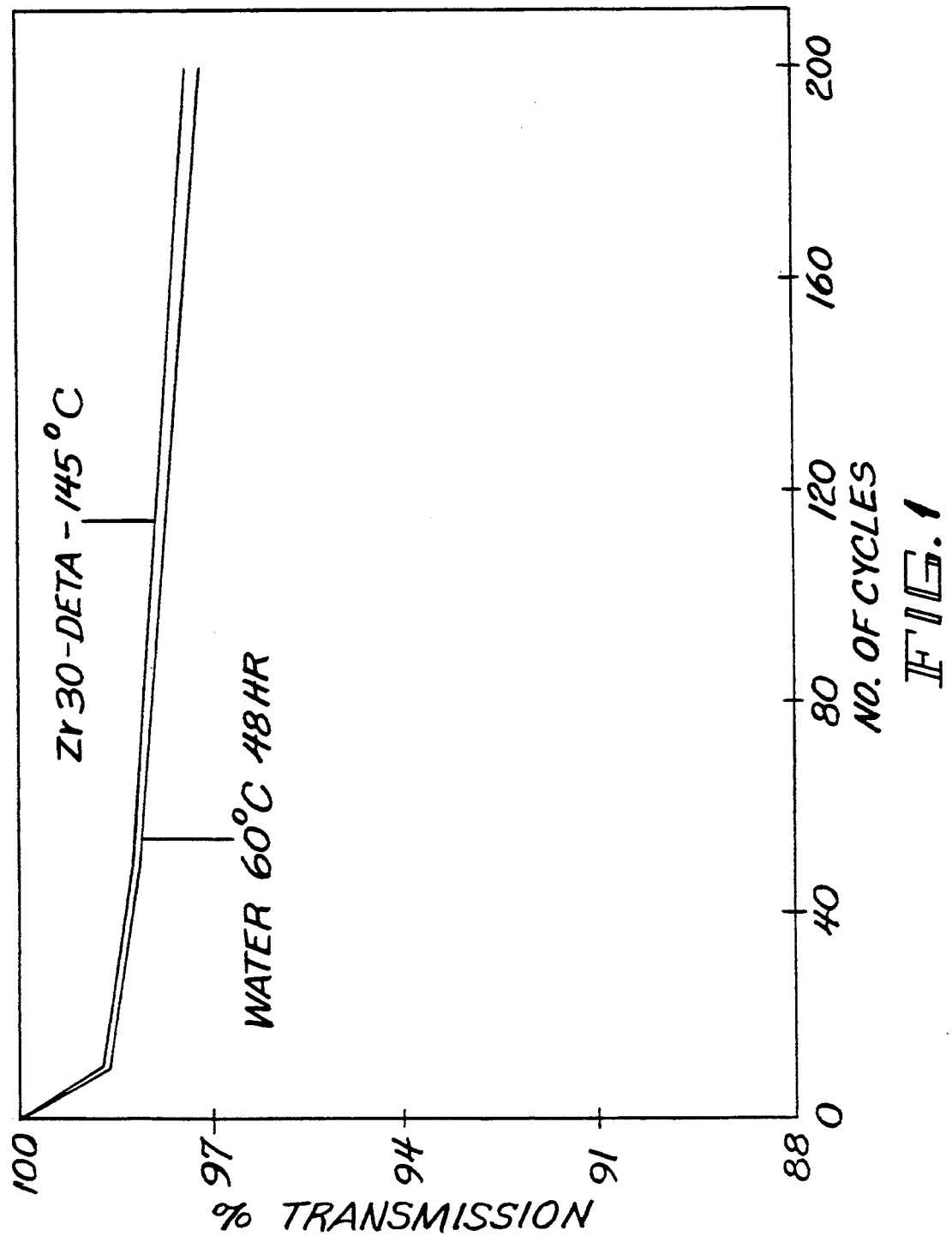

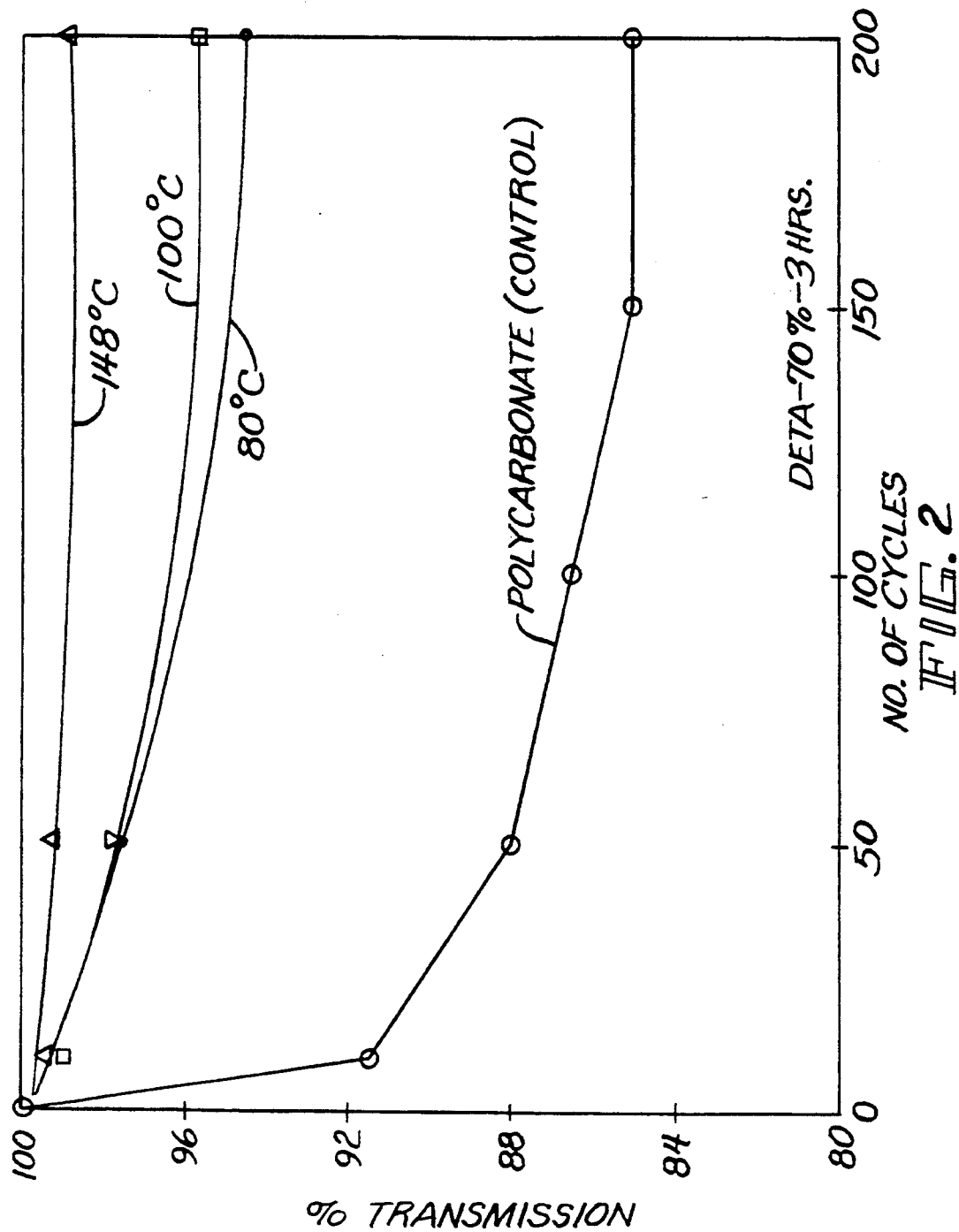

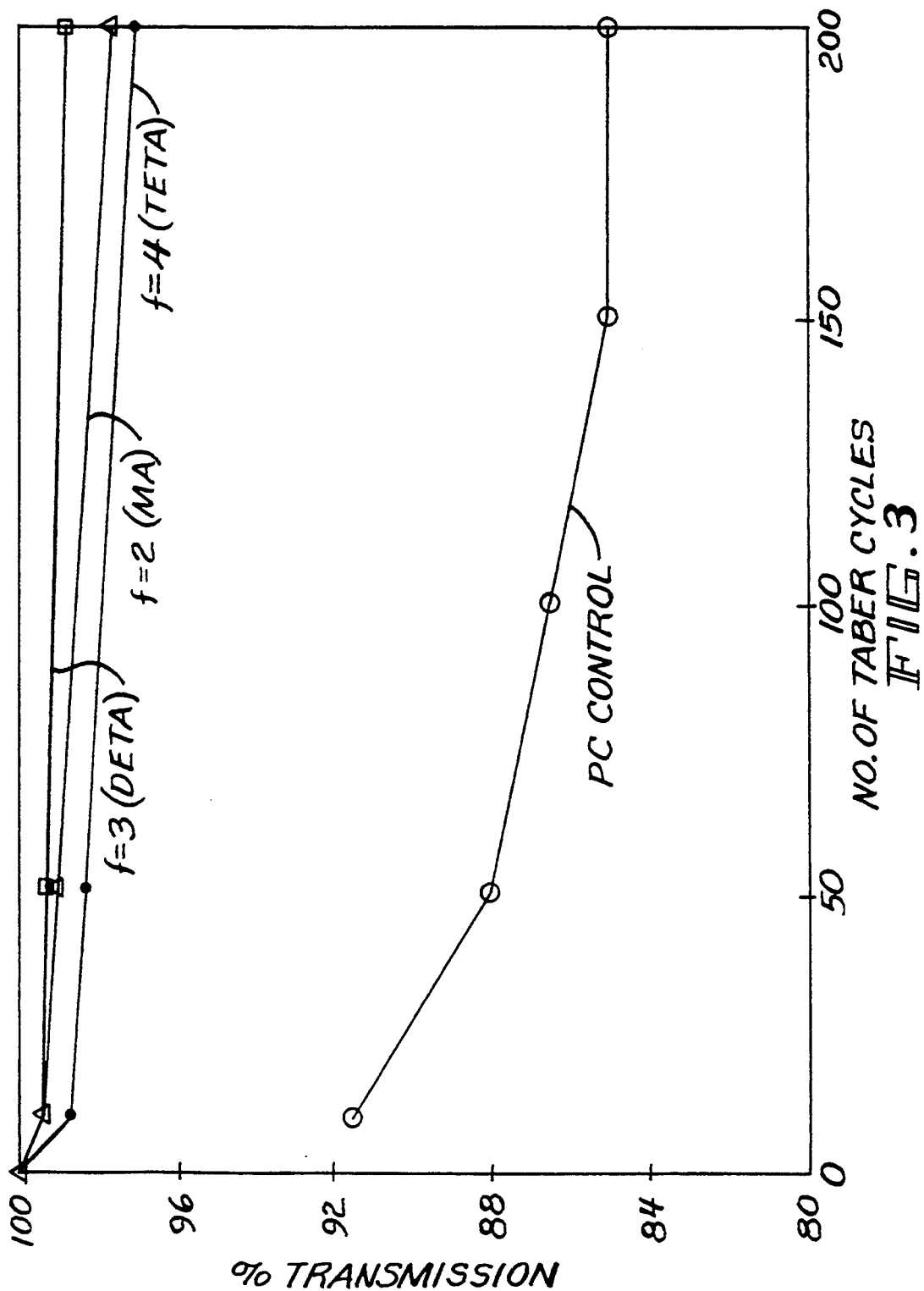

1

FULLY ALKOXYSILANE-FUNCTIONALIZED ALIPHATIC POLYAMINE COMPOUNDS

BACKGROUND OF THE INVENTION

It is known to use sol-gel hydrolyzation/condensation procedures with a reaction mixture comprising one or more metal alkoxide(s) and a trialkoxysilane-functionalized organic reagent to form organic/inorganic hybrid materials having interesting properties. Some recent publications which are representative of work in this area include: Huang, H. et al., Macromolecules. 1987 20(6), 1322; Huang, H. et al., ACS Symposium Series, 1987, 360, 354; and Huang, H. et al., Polym. Bull., 1987, 18, 455. There is interest in expanding the area of known organic/inorganic hybrid systems to novel combinations.

Certain disclosures also exist in the art regarding alkoxysilane-functionalized aliphatic polyamine compounds:

U.S. Pat. No. 3,847,860 shows compounds in which the amino groups are not fully functionalized with alkoxysilane groups for use in relatively minor amount (0.02%–3%) in a cold setting or thermosetting adhesive.

U.S. Pat. No. 4,448,694 also shows compounds in which less than all the amino groups are functionalized with alkoxysilane moieties. These compounds are described for use as chelants for metals after being immobilized on an inorganic solid.

U.S. Pat. No. 4,791,214 and British Patent No. 1,458,533 show "hybrid" compounds containing an alkoxysilane-functionalized amine group and either a glycidyl group or an N-substituted amino group. These compounds are used as bonding agents or adhesion promoters in resin compositions or organic adhesives.

SUMMARY OF THE INVENTION

The present invention is directed to a novel class of fully alkoxysilane-functionalized aliphatic polyamine compounds that are useful, for example, as the predominant reagent in the aforementioned type of sol-gel reactible compositions as sources of the organic moieties (or domains) in organic/inorganic hybrid materials.

This class of reagent can be cured, without the additional presence of a metal alkoxide, such as a tetralkylsilicate or zirconium alkoxide, to form hybrid organic/inorganic materials generally analogous to the previously described materials reported in the Huang et al. publications described before.

DESCRIPTION OF THE DRAWINGS

The Drawings enclosed herewith as part of the present invention illustrate certain embodiments of the invention wherein:

FIG. 1 is a graphical representation of the wear resistance for a 30% zirconium isopropoxide-70% triethoxysilane-capped diethylenetriamine (DETA) material when cured at 145° C. and when such a cured material is allowed to remain in water for forty-eight hours at 60° C. then dried and tested;

FIG. 2 is a plot of the wear of a series of compositions, such as tested in FIG. 1, on polycarbonate resin showing the effect of different curing temperatures for the coating; and FIG. 3 is a plot of the effect of triethoxysilane functionality for a coating derived from a series of alkoxy silane-functionalized aliphatic polyamine compounds.

DETAILED DESCRIPTION OF THE INVENTION

As used herein the term "fully alkoxysilane-functionalized" is intended to connote that the number of alkoxysilane moieties and reacted amine moieties in the functionalized product are substantially equal. In other words, substantially all the amine groups (—NH or —NH$_2$, if terminal) have been functionalized with alkoxysilane groups. The term "aliphatic" as used herein is intended to cover moieties which include alkylene groups (CH$_2$), and, in the case of the diamine compound shown in Example 8, below, the group >C=O.

The aliphatic polyamine compounds which are appropriately functionalized by means of the present invention may have the formula:

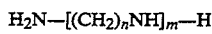

$$H_2N-[(CH_2)_nNH]_m-H$$

where n can be 2, 3 or 4 and m can vary from 1 to about 30. A particularly preferred compound has m and n both equal to 2 and is a triamine. Another aliphatic polyamine compound useful in accordance with the present invention has the formula:

$$H_2N-C(O)-NH_2.$$

The foregoing type of compounds are functionalized by reaction with a compound having an amine-reactive group ("A") at one end (such as an isocyanate group) and an alkoxysilane group at the other. In the case of trialkoxysilane-containing compounds, which are preferred, this compound for use in functionalizing the polyamine will have the general structure:

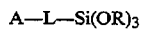

$$A-L-Si(OR)_3$$

where A is the amine-reactive function, L is a linking group, and R is lower alkyl. One class of compound which can be used are the isocyanatoalkylalkoxysilanes wherein the isocyanato moiety reacts with the amine functions in the polyamine forming urethane bonds (e.g., compounds of the formula (RO)$_3$Si(CH$_2$)$_m$N=C=O, where R is a lower alkyl and m can vary from 1 to 4).

The functionalized aliphatic polyamine compounds described herein can be used to form coatings for wear resistance applications in conjunction with metal alkoxides or, surprisingly, alone to form organic/inorganic hybrid materials. In accordance with the present invention, the aliphatic polyamine compounds are present in predominant amount in the compositions used to form the organic/inorganic hybrid materials previously described. Generally, the amount of aliphatic polyamine compound can constitute about 70% or more of such a composition, on a weight basis, and may constitute substantially the entire content of the composition. The alkoxysilane functionalized polyamine compounds are converted to the desired organic/inorganic hybrid materials by conventional sol-gel hydrolysis and condensation procedures in which the alkoxysilane functionalities are treated, usually in the presence of acidic catalysis to dehydrolytically cocondense such alkoxysilane groups into silica rich domains.

If desired, the curing of the desired materials can be accelerated using microwave treatment. In addition, if the cured coating of the alkoxysilane-functionalized aliphatic polyamine is to be placed on a polymeric substrate, this substrate can be treated to a plasma pretreatment (e.g., 50 W to 100 W at times of from several seconds up to about 30 minutes) to enhance the adhesion of such a coating.

The present invention is illustrated by the Examples which follow.

EXAMPLE 1

This Example illustrates preparation of a triethoxysilane-capped diethylenetriamine (DETA).

First, 5 gm of DETA was mixed with 20 gm of isopropanol. Then, 40 gm of 3-isocyanatopropyltriethoxysilane was slowly added to this solution and was stirred for three hours to yield the desired product which was of the formula:

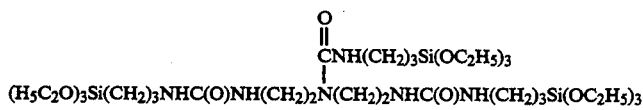

EXAMPLE 2

This Example illustrates preparation of a Ti-DETA sol for use in forming a wear resistant coating.

First, 0.1 ml of HCl (10N), 0.6 ml of $H_2O$, and 5 gm of isopropanol were mixed together in a flask. Then the alcohol solution was transferred to an addition funnel. Next, the HCl-containing isopropanol was slowly added to a polypropylene flask which contained 5 gm of titanium tetraisopropoxide. In order to avoid local inhomogeneity, a slow addition rate of the HCl-containing isopropanol solution and a fast stirring rate were utilized. This procedure developed a clear titania sol (pH=2.2). Then, a solution containing an appropriate amount of triethoxysilane-capped DETA was mixed with the titanium sol and stirring was continued for twenty-seven hours to obtain a viscous homogeneous system for coating on polymeric surfaces (e.g. polycarbonate, polyimide, etc.) by either a dip or spin coating procedure. After drying in an oven at 60° C. for four hours, these coated samples were annealed (cured) at a minimum of 120° C.

EXAMPLE 3

This Example illustrates preparation of a Zr-DETA sol for coatings.

First, 0.1 ml of HCl (10N), and 5 gm of isopropanol were mixed together in a flask. Then the solution was transferred to an addition funnel. Next, the HCl-containing isopropanol was slowly added to a polypropylene flask which contained 5 gm of zirconium tetraisopropoxide. In order to avoid local inhomogeneity, a slow addition rate of the HCl-containing isopropanol solution was maintained and a fast stirring rate was utilized. This procedure developed a clear zirconia sol (pH=2.2). Then, a solution containing an appropriate amount of triethoxysilane-capped DETA was mixed with the zirconium sol and stirring was continued for twenty-seven hours to obtain a viscous homogeneous system for coatings on polymeric surfaces (e.g. polycarbonate, polyimide, etc.) by either a dip or spin coating procedure. After drying in an oven at 60° C. for four hours, these coated samples were annealed (cured) at a minimum of 120° C.

EXAMPLE 4

A sheet of isotactic poly (4-methyl-1-pentene), termed "PMP", which was 3.5 by 3.5 inches square and 1/16 inch in thickness was wiped with ethanol soaked KIM-WIPE fabric. The sheets were then dried with the same dry fabric to insure that the surface was dry. Next, this sample was placed in a plasma chamber and pumping was commenced to reach a vacuum of less than 2 torr. Before turning on the plasma, the gas line was flushed for five minutes with oxygen. Then, the plasma source was turned on for five minutes. Following the plasma treatment, the polymer substrate was coated with a zirconium-containing organic/inorganic based sol which also contained moieties derived from the triethoxysilane-functionalized diethylenetriamine of Example 1. Example 3 illustrates formation of the Zr-DETA sol.

The following results were obtained in regard to abrasion resistance using the type of test described in Example 6 for a 30 wt % zirconium isopropoxide-70% functionalized DETA-derived coating which was cured at 145° C. on plasma pretreated PMP:

| Wheel Cycles | PMP Alone | PMP with Cured Coating |
| --- | --- | --- |
| 10 | 76.1 ± 3.3 | 98.3 ± 0.3 |
| 50 | 67.6 ± 2.5 | 96.3 ± 0.5 |

EXAMPLE 5

This Example reports data analogous to that of Example 6 for a hybrid coating formed from 30 wt % zirconium isopropoxide and 70 wt % trialkoxysilane-functionalized diethylene triamine on polycarbonate using a peel adhesion tape test using 3M-610 brand tape, the tape being applied to the substrate with finger pressure to insure good contact with essentially no dwell time, at a 1 cm/min peeling rate with the adhesion (W) being calculated by the formula $W = P(1-\cos\theta)$ with P being the peeling force per unit width and $\theta$ the peeling angle (180°).

| Pretreatment/Cure Temp | Adhesion (N/m) | |
| --- | --- | --- |
| | High | Low |
| None/60° C. | 35 | 27 |
| None/125° C. | 116 | 111 |
| None/145° C. | 128 | 122 |
| $O_2$-100W-5 min./145° C. | 139 | 131 |

EXAMPLE 6

This Example and FIG. 1 illustrate the results of a visible light measure transmission test on the wear area of a coated polycarbonate sample that had undergone a Taber abrasion test at a load of 250 gm on each wheel using ASTM Taber wheel CS10. The light beam was 0.4×10 mm and the wavelength was 420 nm.

The first coating was formed by curing, at 145° C., a 30 wt % zirconium isopropoxide-70% triethoxysilane-functionalized coating made by the procedure of Example 3, above. The second coating tested was the previously described cured coating which had been allowed to remain in hot (60° C.) water for forty-eight hours followed by drying and testing.

Little difference was noted in the wear behavior of the two samples as shown in FIG. 1.

EXAMPLE 7

FIG. 2 illustrates the wear performance of a coating of the compositional type described in Example 6 which had been cured at 80° C., 100° C., and 146° C., respectively, for three hours. Better wear performance was observed for higher curing temperatures with all being significantly better than an uncoated polycarbonate control.

EXAMPLE 8

FIG. 3 shows the performance of the wear performance of three trialkoxysilane-functionalized monomers as set forth below:

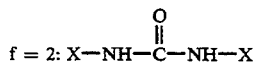

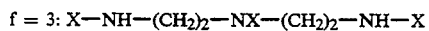

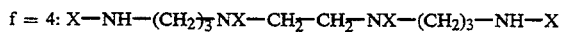

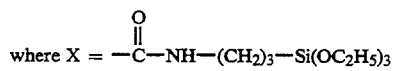

where X = 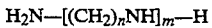

Coatings containing all three as the sole component (no metal alkoxide was present) showed significantly better wear than a polycarbonate (pc) control.

The foregoing are intended to illustrate certain embodiments of the invention and should not therefore be construed in a limiting sense. The scope of protection sought is set forth in the claims which follow.

We claim:

1. A fully alkoxysilane-functionalized aliphatic polyamine compound.

2. A compound as claimed in claim 1 formed by reaction of an aliphatic polyamine with a compound comprising an amine-reactive group and an alkoxysilane group.

3. A compound as claimed in claim 2 wherein the aliphatic polyamine is of the formula:

$$H_2N-[(CH_2)_nNH]_m-H$$

where m can range from 1 to about 30 and n can be 2, 3 or 4.

4. A compound as claimed in claim 3 wherein the aliphatic polyamine is a dialkylenetriamine and is reacted with an isocyanatoalkylalkoxysilane.

5. A compound as claimed in claim 4 wherein the dialkylenetriamine is diethylenetriamine.

6. A fully alkoxysilane-functionalized dialkylenetriamine formed by reaction of diethylenetriamine and 3-isocyanatopropyltriethoxysilane.

7. Hybrid organic/inorganic materials formed by curing a predominant amount of any of the compounds of claim 1.

8. Materials as claimed in claim 7 wherein microwave curing is used.

9. Materials as claimed in claim 7 formed by curing a fully alkoxysilane-functionalized dialkylenetriamine formed by reaction of a diethylenetriamine and an isocyanatoalkylalkoxysilane.

* * * * *